US011006901B2

(12) United States Patent
Gong et al.

(10) Patent No.: US 11,006,901 B2
(45) Date of Patent: May 18, 2021

(54) METHOD, SYSTEM, AND MONITOR FOR DYNAMICALLY DISPLAYING A CHANGE OF A PARAMETER MEASURED AT AN INTERVAL

(71) Applicant: SHENZHEN MINDRAY BIO-MEDICAL ELECTRONICS CO., LTD., Shenzhen (CN)

(72) Inventors: Yunyun Gong, Shenzhen (CN); Lei Qing, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 217 days.

(21) Appl. No.: 15/950,431

(22) Filed: Apr. 11, 2018

(65) Prior Publication Data
US 2019/0110760 A1    Apr. 18, 2019

Related U.S. Application Data

(63) Continuation of application No. PCT/CN2015/091775, filed on Oct. 12, 2015.

(51) Int. Cl.
*A61B 5/00* (2006.01)
*A61B 5/1455* (2006.01)
(Continued)

(52) U.S. Cl.
CPC .............. *A61B 5/742* (2013.01); *A61B 5/02* (2013.01); *A61B 5/0205* (2013.01); *A61B 5/029* (2013.01);
(Continued)

(58) Field of Classification Search
CPC ......... A61B 5/742; A61B 5/02; A61B 5/0205; A61B 5/029; A61B 5/0537; A61B 5/08;
(Continued)

(56) References Cited

U.S. PATENT DOCUMENTS

2009/0024008 A1* 1/2009 Brunner ................. A61B 5/743
                                                  600/301
2011/0077462 A1* 3/2011 Saitou .................... A61B 1/063
                                                  600/109
(Continued)

FOREIGN PATENT DOCUMENTS

CN    101203172    6/2008
CN    101272734    9/2008
(Continued)

*Primary Examiner* — Paula J Stice
(74) *Attorney, Agent, or Firm* — Kory D. Christensen

(57) ABSTRACT

A method for dynamically displaying a change of a parameter measured at an interval comprises: dynamically monitoring at least one type of hemodynamic parameters of a patient by means of a sensor on a monitor; obtaining a first monitoring value of the type of hemodynamic parameters monitored at a first monitoring time; displaying a first form corresponding to the first monitoring value in a simulated graph corresponding to each type of the hemodynamic parameters on a graphic display interface; obtaining a second monitoring value of the type of hemodynamic parameters monitored at a second monitoring time, and determining a second form of the corresponding simulated graph; and adjusting the simulated graph corresponding to each type of hemodynamic parameter from the first form to the second form on the graphic display interface. Also provided are a corresponding system and a dynamic monitor.

18 Claims, 7 Drawing Sheets

(51) Int. Cl.
  *A61B 5/02*    (2006.01)
  *A61B 5/0205*  (2006.01)
  *A61B 5/0537*  (2021.01)
  *A61B 5/029*   (2006.01)
  *A61B 5/08*    (2006.01)

(52) U.S. Cl.
  CPC .............. *A61B 5/0537* (2013.01); *A61B 5/08* (2013.01); *A61B 5/14551* (2013.01); *A61B 5/743* (2013.01); *A61B 5/7475* (2013.01); *A61B 2505/03* (2013.01)

(58) Field of Classification Search
  CPC ... A61B 5/14551; A61B 5/743; A61B 5/7475; A61B 2505/03
  See application file for complete search history.

(56) References Cited

U.S. PATENT DOCUMENTS

| | | | |
|---|---|---|---|
| 2012/0071771 A1 | 3/2012 | Behar | |
| 2012/0179013 A1* | 7/2012 | Saito | A61B 1/00009 600/339 |
| 2013/0324804 A1* | 12/2013 | McKeown | A61B 5/044 600/300 |
| 2016/0058349 A1* | 3/2016 | Morimoto | A61B 1/0669 600/327 |

FOREIGN PATENT DOCUMENTS

| | | |
|---|---|---|
| CN | 101385641 | 3/2009 |
| EP | 2881034 | 6/2015 |

\* cited by examiner

METHOD, SYSTEM, AND MONITOR FOR DYNAMICALLY DISPLAYING A CHANGE OF A PARAMETER MEASURED AT AN INTERVAL

CROSS REFERENCE TO RELATED APPLICATIONS

This application is a continuation of PCT Application No. PCT/CN2015/091775, filed Oct. 12, 2015, for METHOD, SYSTEM, AND MONITOR FOR DYNAMICALLY DISPLAYING A CHANGE OF A PARAMETER MEASURED AT AN INTERVAL, which is incorporated herein by reference.

TECHNICAL FIELD

The present disclosure relates to medical monitoring, and more particularly to a method, a system, and a monitor for dynamically displaying a change of a medical parameter, such as a hemodynamic parameter, measured at an interval.

BACKGROUND

Patients may need to have hemodynamic parameters monitored in an intensive care unit (ICU) or in cases of longer-term monitoring. However, in existing hemodynamic monitors, only changes of a hemodynamic parameter of a patient in a short period of time can be observed. For changes of the hemodynamic parameter in a longer period of time, e.g., before and after a surgery, the changes cannot be visually checked by the existing dynamic monitors, and medical care personnel need to spend time comparing data to obtain the changes of the hemodynamic parameter of the patient and then determine a course of action for the patient's treatment and recovery.

SUMMARY

The present disclosure provides a method, a system, and a monitor for dynamically displaying a change of a parameter measured at an interval, so that dynamic changes of the parameter can be displayed visually and graphically.

One embodiment of the present disclosure provides a method for dynamically displaying a change of a measured parameter, including: monitoring at least one type of hemodynamic parameters of a patient by means of a sensor on a monitor and storing the type of hemodynamic parameters monitored; obtaining a first monitoring value of the type of hemodynamic parameters monitored at a first monitoring time; configuring a simulated graph corresponding to each type of hemodynamic parameter on a graphic display interface, and displaying a first morphology of the corresponding simulated graph according to the first monitoring value of the type of hemodynamic parameters monitored; obtaining a second monitoring value of the type of hemodynamic parameters monitored at a second monitoring time, and determining a second morphology of the corresponding simulated graph according to the second monitoring value; and dynamically adjusting the simulated graph corresponding to the type of hemodynamic parameters monitored from the first morphology to the second morphology on the graphic display interface.

The hemodynamic parameter may include at least one of the global end-diastolic volume index (GEDI), systemic vascular resistance index (SVRI), extravascular lung water index (ELWI), and oxygen saturation level.

The simulated graph corresponding to the global end-diastolic volume index (GEDI) may be is configured as a cardiac contour graph. The simulated graph corresponding to the extravascular lung water index (ELWI) may be configured as a lung graph with lung water. The simulated graph corresponding to the systemic vascular resistance index (SVRI) may be configured as a tubular cross-section graph. The simulated graph corresponding to the oxygen saturation level may be configured as a blood vessel graph.

Configuring a simulated graph corresponding to each type of hemodynamic parameter on a graphic display interface and displaying the first morphology of the corresponding simulated graph according to the first monitoring value of the type of hemodynamic parameters monitored may further include at least one of the following steps: adjusting a size of the cardiac contour in the corresponding simulated graph to a corresponding first size according to the first monitoring value of the global end-diastolic volume index (GEDI), and displaying the first size of the cardiac contour; adjusting a height of a horizontal plane of the lung water in the corresponding simulated graph to a corresponding first height, according to the first monitoring value of the extravascular lung water index (ELWI), and displaying the first height of the horizontal plane of the lung water; adjusting a diameter of the tubular cross-section in the corresponding simulated graph to a corresponding first diameter according to the first monitoring value of the systemic vascular resistance index (SVRI), and displaying the first diameter of the tubular cross-section; and adjusting a color of the blood vessel in the corresponding simulated graph to a corresponding first color according to the first monitoring value of the oxygen saturation level, and displaying the first color of the blood vessel.

The step of obtaining a second monitoring value of the type of hemodynamic parameters monitored at a second monitoring time and determining a second morphology of the corresponding simulated graph according to the second monitoring value may include at least one of the following steps: determining a second size corresponding to the cardiac contour in the corresponding simulated graph, according to a second monitoring value of the global end-diastolic volume index (GEDI); determining a second height corresponding to the height of the horizontal plane of the lung water in the corresponding simulated graph, according to a second monitoring value of the extravascular lung water index (ELWI); determining a second diameter corresponding to the tubular cross-section in the corresponding simulated graph, according to a second monitoring value of the systemic vascular resistance index (SVRI); and determining a second color corresponding to the blood vessel in the corresponding simulated graph, according to a second monitoring value of the oxygen saturation level.

The step of dynamically adjusting the simulated graph corresponding to the type of hemodynamic parameters monitored from the first morphology to the second morphology on the graphic display interface may include at least one of the following steps: dynamically adjusting the size of the cardiac contour from the first size to the second size, in the simulated graph corresponding to the global end-diastolic volume index (GED); dynamically adjusting the height of the horizontal plane of the lung water from the first height to the second height, in the simulated graph corresponding to the extravascular lung water index (ELWI); dynamically adjusting the diameter of the tubular cross-section from the first diameter to the second diameter, in the simulated graph corresponding to the systemic vascular resistance index (SVRI); and dynamically adjusting the color of the blood vessel from the first color to the second color, in the simulated graph corresponding to the oxygen saturation level. The dynamic adjustment may be implemented, for example, through animation.

In one embodiment, the method may further include prestoring various morphologies of the simulated graphs corresponding to the monitoring values of each type of hemodynamic parameter.

In some embodiments, the method may further includes predetermining a normal value of each type of hemodynamic parameter, and marking a reference morphology corresponding to the normal value in the simulated graph corresponding to each type of hemodynamic parameter on the graphic display interface.

In various embodiments, the method further includes presetting a time interval between the first monitoring time and the second monitoring time, and after one dynamic adjustment, automatically performing a next dynamic adjustment action when the time interval is reached.

In certain embodiments, the method further includes manually determining the first monitoring time and the second monitoring time.

One embodiment of the present disclosure further provides a system for dynamically displaying a change of a parameter measured at an interval, including: a dynamic monitoring unit for dynamically monitoring at least one type of hemodynamic parameters of a patient by means of a sensor on a dynamic monitor and storing the type of hemodynamic parameters monitored; a first monitoring value obtaining unit for obtaining a first monitoring value of the type of hemodynamic parameters monitored at a first monitoring time; a first morphology display unit for configuring a simulated graph corresponding to each type of hemodynamic parameter on a graphic display interface and displaying a first morphology of the corresponding simulated graph according to the first monitoring value of the type of hemodynamic parameters monitored; a second morphology determination unit for obtaining a second monitoring value of the type of hemodynamic parameters monitored at a second monitoring time and determining a second morphology of the corresponding simulated graph according to the second monitoring value; and a dynamic adjustment unit for dynamically adjusting the simulated graph corresponding to the type of hemodynamic parameters monitored from the first morphology to the second morphology on the graphic display interface.

The hemodynamic parameter may include at least one of the global end-diastolic volume index (GEDI), systemic vascular resistance index (SVRI), extravascular lung water index (ELWI) and oxygen saturation level, wherein the simulated graph corresponding to the global end-diastolic volume index (GEDI) is configured as a cardiac contour graph, the simulated graph corresponding to the extravascular lung water index (ELWI) is configured as a lung graph with lung water, the simulated graph corresponding to the systemic vascular resistance index (SVRI) is configured as a tubular cross-section graph, and the simulated graph corresponding to the oxygen saturation level is configured as a blood vessel graph.

In one embodiment, the first morphology display unit further includes at least one of: a GEDI simulated display unit for adjusting a size of the cardiac contour in the corresponding simulated graph to a corresponding first size, according to the first monitoring value of the global end-diastolic volume index (GEDI) and displaying the first size of the cardiac contour; an ELWI simulated display unit for adjusting a height of a horizontal plane of the lung water in the corresponding simulated graph to a corresponding first height according to the first monitoring value of the extravascular lung water index (ELWI) and displaying the first height of the horizontal plane of the lung water; an SVRI simulated display unit for adjusting a diameter of the tubular cross-section in the corresponding simulated graph to a corresponding first diameter according to a first monitoring value of the systemic vascular resistance index (SVRI) and displaying the first diameter of the tubular cross-section; and an oxygen saturation level simulated display unit for adjusting a color of the blood vessel in the corresponding simulated graph to a corresponding first color according to the first monitoring value of the oxygen saturation level and displaying the first color of the blood vessel.

In some embodiments, the second morphology determination unit includes at least one of: a second GEDI morphology determination unit for determining a second size corresponding to the cardiac contour in the corresponding simulated graph according to the second monitoring value of the global end-diastolic volume index (GEDI); a second ELWI morphology determination unit for determining a second height corresponding to the height of the horizontal plane of the lung water in the corresponding simulated graph according to the second monitoring value of the extravascular lung water index (ELWI); a second SVRI morphology determination unit for determining a second diameter corresponding to the tubular cross-section in the corresponding simulated graph according to the second monitoring value of the systemic vascular resistance index (SVRI); and a second oxygen saturation level morphology determination unit for determining the second color corresponding to the blood vessel in the corresponding simulated graph according to a second monitoring value of the oxygen saturation level.

In various embodiments, the dynamic adjustment unit includes at least one of: a GED dynamic adjustment unit for dynamically adjusting the size of the cardiac contour from the first size to the second size, in the simulated graph corresponding to the global end-diastolic volume index (GED); an ELWI dynamic adjustment unit for dynamically adjusting the height of a horizontal plane of the lung water from the first height to the second height, in the simulated graph corresponding to the extravascular lung water index (ELWI); an SVRI dynamic adjustment unit for dynamically adjusting the diameter of the tubular cross-section from the first diameter to the second diameter, in the simulated graph corresponding to the systemic vascular resistance index (SVRI); and an oxygen saturation level dynamic adjustment unit for dynamically adjusting the color of the blood vessel from the first color to the second color, in the simulated graph corresponding to the oxygen saturation level.

In certain embodiments, the dynamic adjustment unit implements the dynamic adjustment through animation.

In some embodiments, the system further includes a storage unit for prestoring various morphologies of the simulated graphs corresponding to the monitoring values of each type of hemodynamic parameter.

In various embodiments, the system further includes a reference morphology marking unit for predetermining a normal value of each type of hemodynamic parameter, and marking a reference morphology corresponding to the normal value in the simulated graph corresponding to each type of hemodynamic parameter on the graphic display interface.

The system may further include a time interval setting unit for presetting a time interval between the first monitoring time and the second monitoring time and, after one dynamic adjustment, automatically performing a next dynamic adjustment action when the time interval is reached.

In certain embodiments, the system further includes a monitoring time setting unit for manually determining the first monitoring time and the second monitoring time.

One embodiment of the present disclosure further provides a dynamic monitor including at least the foregoing system for dynamically displaying a change of a parameter measured at an interval.

Another embodiment of the present disclosure further provides a method for displaying a parameter measured at an interval, including the steps of: acquiring a first monitoring value of a parameter at a first monitoring time, and statically displaying the first monitoring value on a monitoring display interface; storing the first monitoring value; acquiring a second monitoring value of the parameter at a second monitoring time after a time interval, displaying on the monitoring display interface a process for the parameter to change from the first monitoring value to the second monitoring value, and subsequently statically displaying the second monitoring value.

After statically displaying the first monitoring value, the method may include exiting the monitoring display interface according to a preset condition or in response to a user operation.

In one embodiment, the method may include entering into the monitoring display interface when or before acquiring the first monitoring value, and displaying a process for the parameter to change dynamically from a historical monitoring value stored in a previous measurement to the first monitoring value after statically displaying the first monitoring value.

In various embodiments, the dynamic change includes one of the following: a sudden change of the monitored value and/or a color change of the monitored value, and a contour, color and/or area change of the simulated graph corresponding to the parameter.

In some embodiments, the parameter includes at least one of the following hemodynamic parameters: a global end-diastolic volume index (GEDI), a systemic vascular resistance index (SVRI), an extravascular lung water index (ELWI), and an oxygen saturation level, and wherein said method further comprises displaying a change of the monitored value via a dynamic change of a simulated graph corresponding to the said hemodynamic parameter.

In various embodiments, the simulated graph corresponding to the global end-diastolic volume index (GEDI) is configured as a cardiac contour graph; the simulated graph corresponding to the extravascular lung water index (ELWI) is configured as a lung graph with lung water; the simulated graph corresponding to the systemic vascular resistance index (SVRI) is configured as a tubular cross-section graph; and the simulated graph corresponding to the oxygen saturation level is configured as a blood vessel graph.

The present disclosure provides a method and a system for dynamically displaying a change of a parameter measured at an interval, in which a simulated graph of each type of hemodynamic parameter is provided on a graphic display interface, and the difference between a previous monitored value and a current monitored value of the hemodynamic parameter at different intervals is shown through changes of shape, color, height and the like in the simulated graph. In this way, medical care personnel can visually and quickly grasp the change of the patient's hemodynamic parameter at different intervals by viewing the graphic display interface, which can assist in determining therapeutic effects on the patient before and after the treatment. Furthermore, a reference morphology corresponding to a normal value of each type of hemodynamic parameter is marked on each simulated graph, so as to further provide reference indication to the medical care personnel.

DETAILED DESCRIPTION

The technical solutions of the embodiments of the present disclosure will be described below clearly and comprehensively in conjunction with the drawings. Those skilled in the art will recognize that the embodiments described are merely exemplary embodiments of the present disclosure and are not all the possible embodiments. Based on the embodiments given in the present disclosure, all other embodiments that would be obtained by those of ordinary skill in the art without expending inventive effort shall be considered within the scope of the present disclosure.

Figure 1:
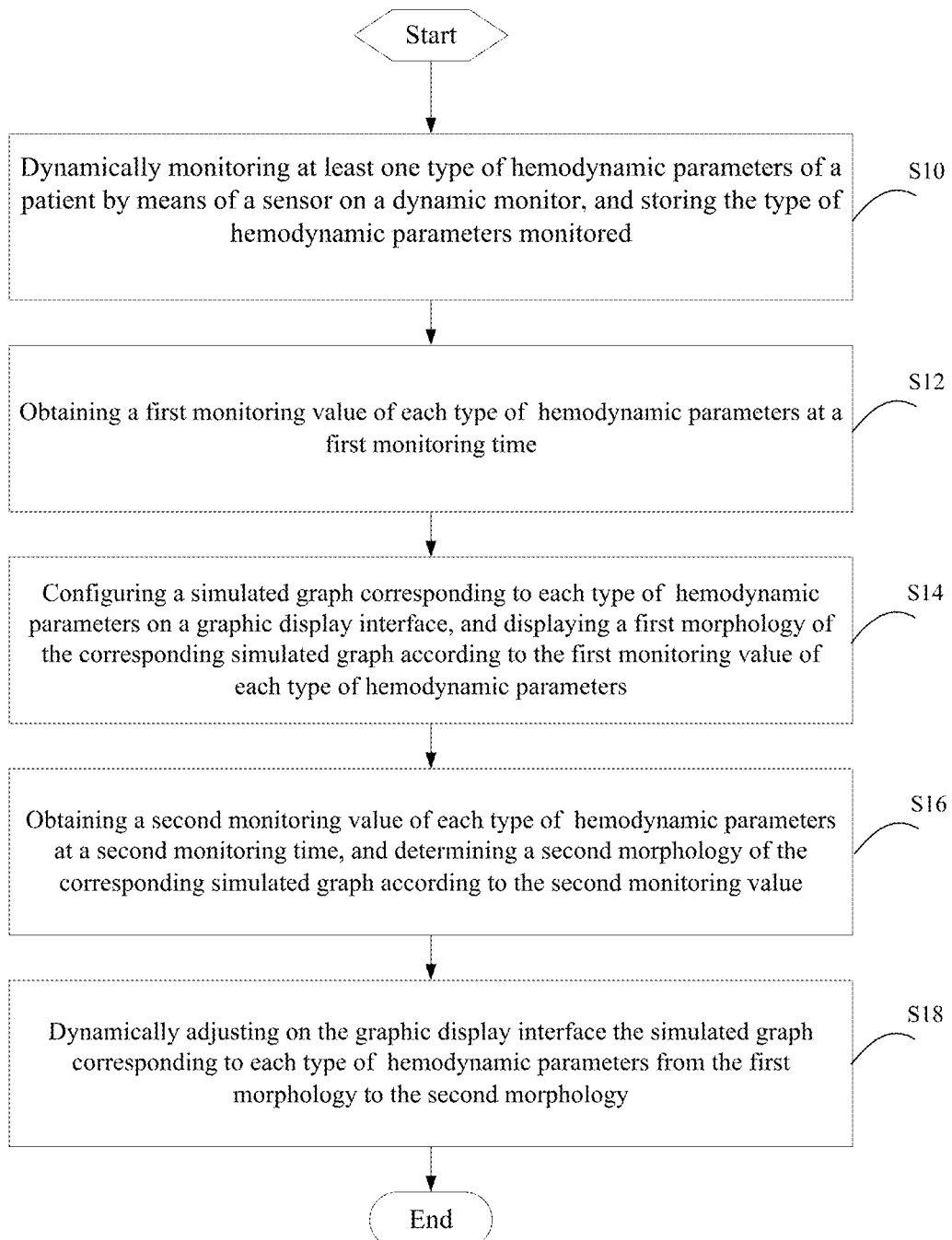
FIG. 1 is a schematic diagram of a main process of a method.

FIG. 1 shows a schematic diagram of a main process of an embodiment of a method for dynamically displaying a change of a parameter measured at an interval provided by the present disclosure. Reference is also made to FIGS. 2 to 4C. In this embodiment, the method for dynamically displaying a change of a parameter measured at an interval includes:

step S10: dynamically monitoring at least one type of hemodynamic parameter of a patient by means of a sensor on a dynamic monitor, and storing the type of hemodynamic parameter monitored, wherein the hemodynamic parameter include at least one of a global end-diastolic volume index (GEDI), a systemic vascular resistance index (SVRI), an extravascular lung water index (ELWI), and an oxygen saturation level;

step S12: obtaining a first monitoring value of each type of hemodynamic parameter at a first monitoring time;

step S14: configuring a simulated graph corresponding to each type of hemodynamic parameter on a graphic display interface, and displaying a first morphology of the corresponding simulated graph according to the first monitoring value of each type of hemodynamic parameter;

step S16: obtaining a second monitoring value of each type of hemodynamic parameter at a second monitoring time, and determining a second morphology of the corresponding simulated graph according to the second monitoring value; and step S18: dynamically adjusting on the graphic display interface the simulated graph corresponding to each type of hemodynamic parameter from the first morphology to the second morphology.

Figure 2:
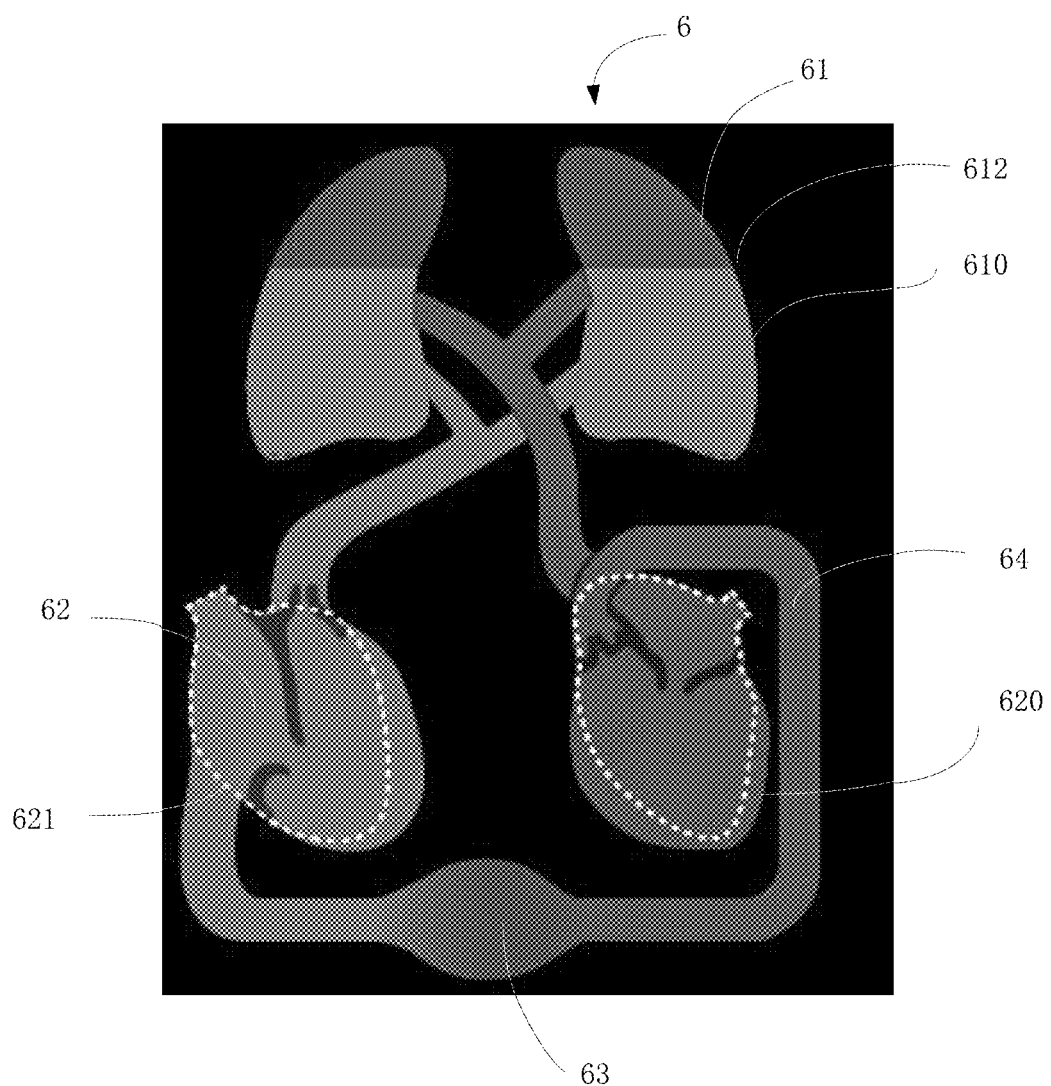
FIG. 2 is a schematic diagram of a graphic display interface in FIG. 1 in one morphology.

As an example, as shown in FIG. 2, on a graphic display interface 6, a simulated graph corresponding to the global end-diastolic volume index (GEDI) is configured as a cardiac contour graph 62; a simulated graph corresponding to the extravascular lung water index (ELWI) is configured as a lung graph 61 with lung water 610 at the bottom; a simulated graph corresponding to the systemic vascular resistance index (SVRI) is configured as a tubular cross-section graph 63; and a simulated graph corresponding to the oxygen saturation level is configured as a blood vessel graph 64.

It can be understood that in the method, various morphologies of the simulated graph corresponding to the monitoring values of each type of hemodynamic parameter may be prestored, so that various monitoring values correspond to the various morphologies of the simulated graph.

Various monitoring values of the global end-diastolic volume index (GEDI) correspond to cardiac contours of various sizes. For example, a greater monitoring value of the global end-diastolic index (GEDI) corresponds to a larger cardiac contour in the simulated graph.

Various monitoring values of the extravascular lung water index (ELWI) correspond to various heights of the horizontal plane of the lung water. For example, a greater monitoring value of the extravascular lung water index (ELWI) corresponds to a higher horizontal plane 612 of the lung water in the simulated graph.

Figures 4A, 4B, 4C:
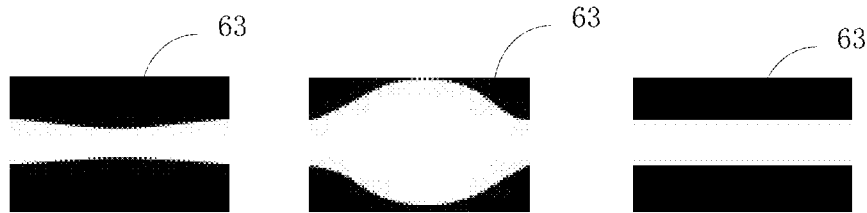
FIGS. 4A, 4B, and 4C are schematic diagrams of three morphologies of a simulated graph corresponding to a systemic vascular resistance index (SVRI) on the graphic display interface in FIG. 1.

Various monitoring values of the systemic vascular resistance index (SVRI) correspond to various diameters (diameter length) of the tubular cross-section. For example, a greater monitoring value of the systemic vascular resistance index (SVRI) corresponds to a smaller tubular cross-section in the simulated graph. For example, FIG. 4A represents a case of vasoconstriction (a greater resistance), FIG. 4B represents a case of vasodilation (a smaller resistance), and FIG. 4C represents a case of a normal blood vessel (a moderate resistance).

Various monitoring values of the oxygen saturation level may correspond to various colors of the blood vessel. For example, a greater monitoring value of the oxygen saturation level may correspond to a deeper color of the blood vessel in the simulated graph.

In one embodiment, step S14 further includes at least the following steps:

adjusting the size of the cardiac contour in the corresponding simulated graph to a corresponding first size, according to the first monitoring value of the global end-diastolic volume index (GEDI), and displaying the first size of the cardiac contour;

adjusting the height of horizontal plane of the lung water in the corresponding simulated graph to a corresponding first height according to the first monitoring value of the extravascular lung water index (ELWI), and displaying the first height of the horizontal plane of the lung water;

adjusting the diameter of the tubular cross-section in the corresponding simulated graph to a corresponding first diameter according to the first monitoring value of the systemic vascular resistance index (SVRI), and displaying the first diameter of the tubular cross-section; and adjusting the color of the blood vessel in the corresponding simulated graph to a corresponding first color according to the first monitoring value of the oxygen saturation level, and displaying the first color of the blood vessel.

Step S16 may include at least one of the following steps:

determining a second size corresponding to the cardiac contour in the corresponding simulated graph, according to the second monitoring value of the global end-diastolic volume index (GEDI);

determining a second height corresponding to the height of the horizontal plane of the lung water, in the corresponding simulated graph according to the second monitoring value of the extravascular lung water index (ELWI);

determining a second diameter corresponding to the tubular cross-section in the corresponding simulated graph according to the second monitoring value of the systemic vascular resistance index (SVRI); and determining a second color corresponding to the blood vessel in the corresponding simulated graph according to the second monitoring value of the oxygen saturation level.

Figure 3:
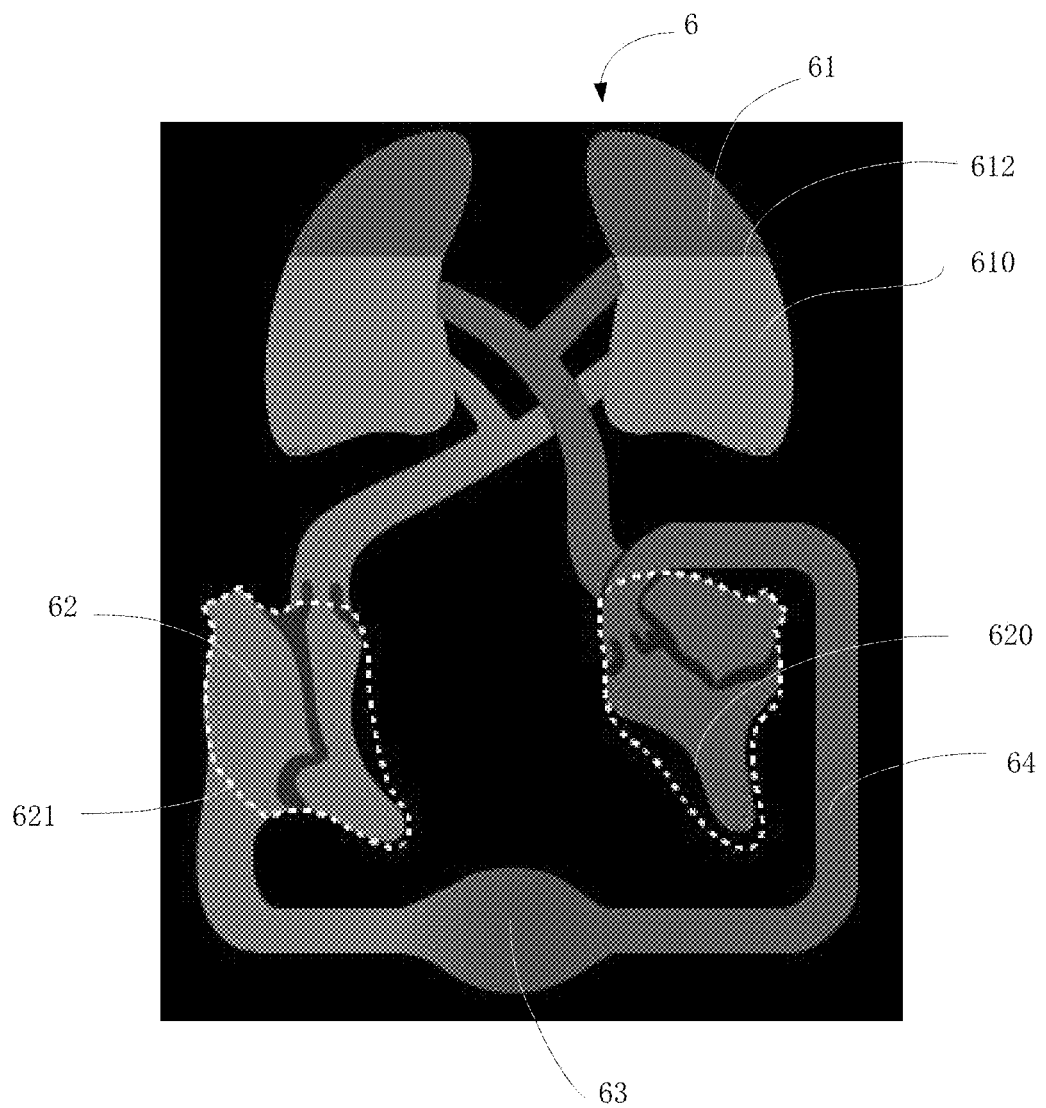
FIG. 3 is a schematic diagram of the graphic display interface in FIG. 1 in another morphology.

Step S18 may include at least one of the following steps:

dynamically adjusting the size of the cardiac contour from the first size to the second size, in the simulated graph corresponding to the global end-diastolic volume index (GED), specifically referring to a change of the cardiac contour 620 in FIGS. 2 to 3.

dynamically adjusting the height of the horizontal plane of the lung water from the first height to the second height, in the simulated graph corresponding to the extravascular lung water index (ELWI);

dynamically adjusting the diameter of the tubular cross-section from the first diameter to the second diameter, in the simulated graph corresponding to the systemic vascular resistance index (SVRI); and dynamically adjusting the color of the blood vessel from the first color to the second color, in the simulated graph corresponding to the oxygen saturation level.

In various embodiments, the dynamic adjustment is implemented through animation.

The change of the parameter measured at an interval may be displayed by automatic refreshing, which may be implemented by presetting a time interval between the first monitoring time and the second monitoring time, and after one dynamic adjustment, automatically performing a next dynamic adjustment action when the time interval is reached.

In this manner, the simulated graph corresponding to each type of hemodynamic parameter is dynamically adjusted from a previous morphology to a latest morphology at regular time intervals.

Additionally, the change of the parameter measured at an interval may also be displayed by manual refreshing, such as by manually determining the first monitoring time and the second monitoring time.

In addition, to conveniently and visually determine whether current monitoring values of the hemodynamic parameter are in a normal range, in some embodiments, a normal value of each type of hemodynamic parameter may be predetermined, and a reference morphology may be marked corresponding to the normal value of the hemodynamic parameter in the simulated graph corresponding to each type of hemodynamic parameter on the graphic display interface. A cardiac contour 621 marked by a dashed line in FIG. 2 is a reference morphology corresponding to the normal value of the global end-diastolic volume index (GED).

Figure 5:
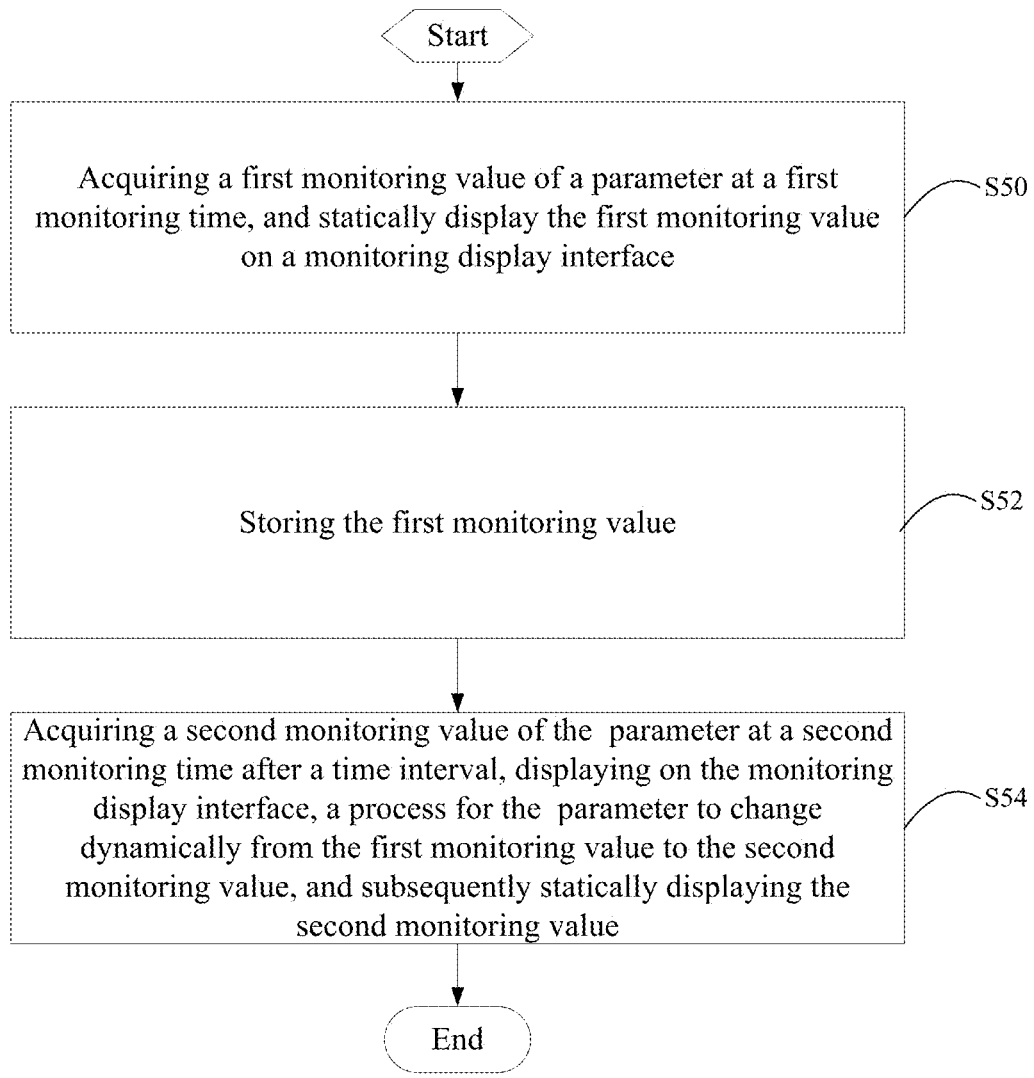
FIG. 5 is a schematic diagram of a main process of a method.

FIG. 5 is a schematic structural diagram of another embodiment of a method for dynamically displaying a change of a parameter measured at an interval provided by the present disclosure. The method may include the steps of:

step S50: acquiring a first monitoring value of a parameter at a first monitoring time, and statically display the first monitoring value on a monitoring display interface;

step S52: storing the first monitoring value; and step S54: acquiring a second monitoring value of the parameter at a second monitoring time after a time interval, displaying on the monitoring display interface, a process for the parameter to change dynamically from the first monitoring value to the second monitoring value, and subsequently statically displaying the second monitoring value; specifically, the dynamic change includes one of: a sudden change of the monitored value and/or a color change of the monitored value, and a contour, color and/or area change of a simulated graph corresponding to the parameter, and so on.

During a monitoring time interval, in a dynamic monitor, the monitoring display interface may be exited and a conventional display interface is returned, that is, after statically displaying the first monitoring value, the monitoring display interface is exited according to a preset condition or in response to a user operation, the preset condition being, for example, a preset time (e.g., five seconds), and the user operation being, for example, an exit operation of the user.

Additionally, the user can manually refresh display content of each type of parameters in a previous monitoring period on the monitoring display interface. For example, entering into the monitoring display interface when or before acquiring the first monitoring value, and displaying a process of the parameter to change dynamically form a historical monitoring value stored in a previous measurement to the first monitoring value before statically displaying the first monitoring value.

In this embodiment, the parameter may include at least one of the following hemodynamic parameters: a global end-diastolic volume index (GEDI), a systemic vascular resistance index (SVRI), an extravascular lung water index (ELWI), and an oxygen saturation level, and displaying a change of monitored value via a dynamic change of the corresponding simulated graphs. The simulated graph corresponding to the global end-diastolic volume index (GEDI) is configured as a cardiac contour graph; the simulated graph corresponding to the extravascular lung water index (ELWI) is configured as a lung graph with lung water; the simulated graph corresponding to the systemic vascular resistance index (SVRI) is configured as a tubular cross-section graph; and the simulated graph corresponding to the oxygen saturation level is configured as a blood vessel graph.

For more details, reference may be made to the above descriptions of FIGS. 1 to 4C, which are not repeated here.

Figure 6:
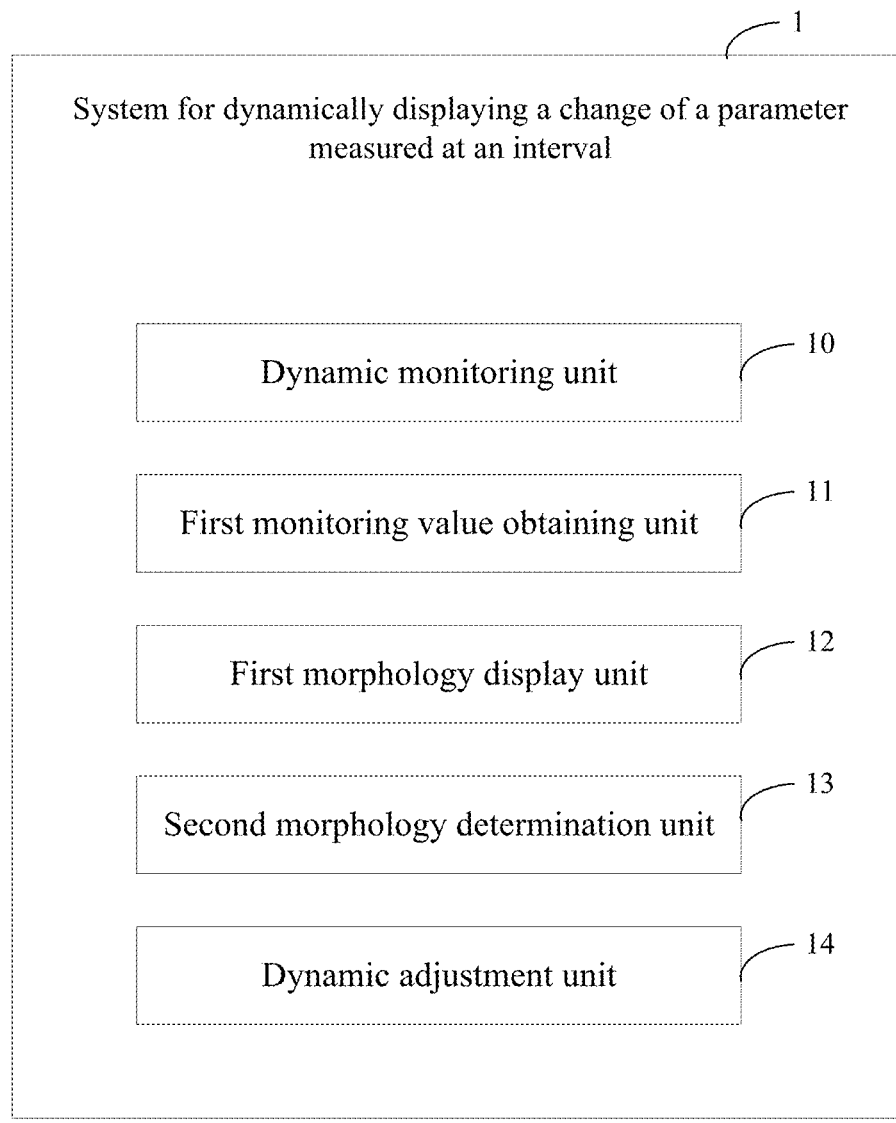
FIG. 6 is a schematic structural diagram of a system.

FIG. 6 is a schematic structural diagram of an embodiment of a system for dynamically displaying a change of a parameter measured at an interval. In this embodiment, the system 1 for dynamically displaying a change of a parameter measured at an interval includes:

a dynamic monitoring unit 10 for dynamically monitoring at least one type of hemodynamic parameters of a patient by means of a sensor on a dynamic monitor, and storing the type of hemodynamic parameters monitored;

a first monitoring value obtaining unit 11 for obtaining a first monitoring value of each type of hemodynamic parameter at a first monitoring time;

a first morphology display unit 12 for configuring a simulated graph corresponding to each type of hemodynamic parameter on a graphic display interface and displaying a first morphology of the corresponding simulated graph according to the first monitoring value of each type of hemodynamic parameter;

a second morphology determination unit 13 for obtaining a second monitoring value of each type of hemodynamic parameter at a second monitoring time and determining a second morphology of the corresponding simulated graph according to the second monitoring value; and a dynamic adjustment unit 14 for dynamically adjusting the simulated graph corresponding to each type of hemodynamic parameter from the first morphology to the second morphology on the graphic display interface.

Figure 7:
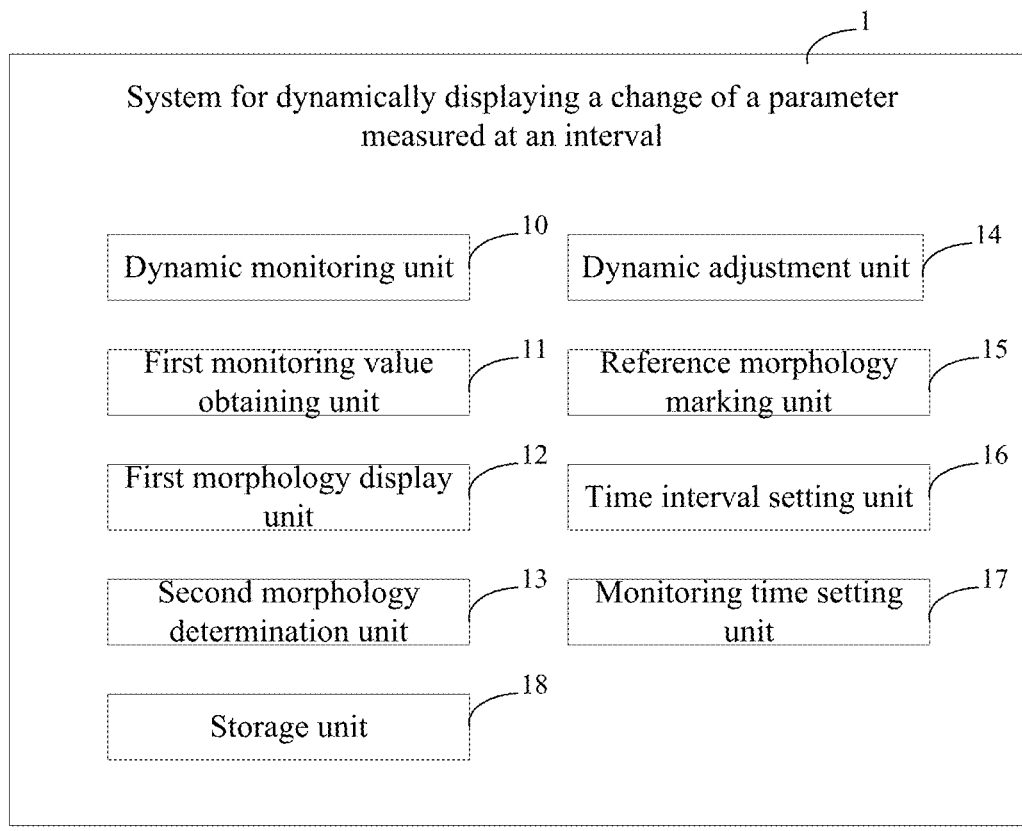
FIG. 7 is a schematic structural diagram of a system.

FIG. 7 is a schematic structural diagram of another embodiment of a system for dynamically displaying a change of a parameter measured at an interval provided by the present disclosure. This embodiment differs from the embodiment shown in FIG. 6 as follows.

A storage unit 18 is used to prestore various morphologies of the simulated graph corresponding to monitoring values of each type of hemodynamic parameter. Specifically, the hemodynamic parameters include at least one of global end-diastolic volume index (GEDI), systemic vascular resistance index (SVRI), extravascular lung water index (ELWI) and oxygen saturation level. The simulated graph corresponding to the global end-diastolic volume index (GEDI) is configured as a cardiac contour graph; the simulated graph corresponding to the extravascular lung water index (ELWI) is configured as a lung graph with lung water; the simulated graph corresponding to the systemic vascular resistance index (SVRI) is configured as a tubular cross-section graph; and the simulated graph corresponding to the oxygen saturation level is configured as a blood vessel graph.

A reference morphology marking unit 15 is used to predetermine a normal value of each type of hemodynamic parameter and mark a reference morphology corresponding to the normal value in the simulated graph corresponding to each type of hemodynamic parameter on the graphic display interface.

A time interval setting unit 16 is used to preset a time interval between the first monitoring time and the second monitoring time, and after one dynamic adjustment, automatically perform a next dynamic adjustment action when the time interval is reached.

A monitoring time setting unit 17 is used to manually determine the first monitoring time and the second monitoring time.

Figure 8:
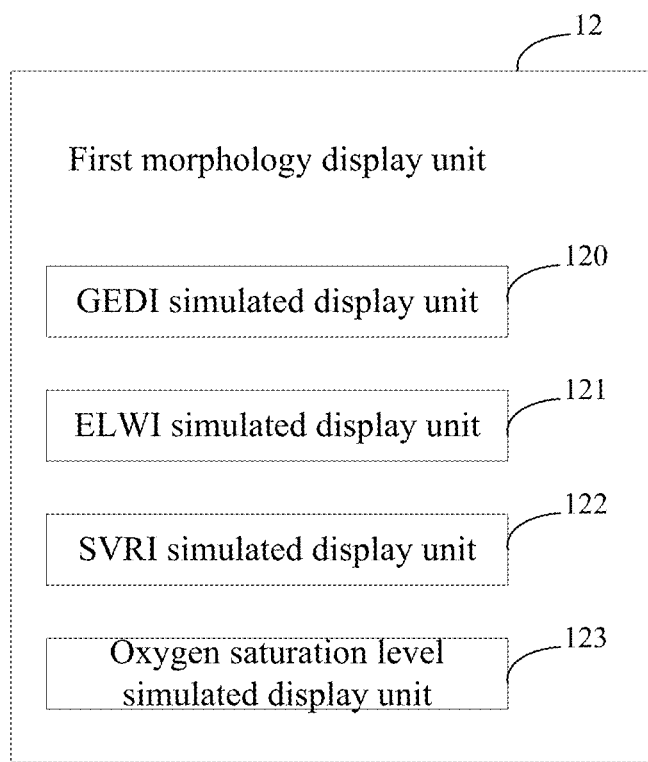
FIG. 8 is a schematic structural diagram of a first morphology display unit in FIG. 6.

Referring to FIG. 8, the first morphology display unit 12 may further include at least one of:

a GEDI simulated display unit 120 for adjusting a size of the cardiac contour in the corresponding simulated graph to a corresponding first size, according to the first monitoring value of the global end-diastolic volume index (GEDI) and displaying the first size of the cardiac contour;

an ELWI simulated display unit 121 for adjusting a height of a horizontal plane of the lung water in the corresponding simulated graph to a corresponding first height according to the first monitoring value of the extravascular lung water index (ELWI) and displaying the first height of the horizontal plane of the lung water;

an SVRI simulated display unit 122 for adjusting a diameter of the tubular cross-section in the corresponding simulated graph to a corresponding first diameter according to the first monitoring value of the systemic vascular resistance index (SVRI) and displaying the first diameter of the tubular cross-section; and an oxygen saturation level simulated display unit 123 for adjusting a color of the blood vessel in the corresponding simulated graph to a corresponding first color according to the first monitoring value of the oxygen saturation level and displaying the first color of the blood vessel.

Figure 9:
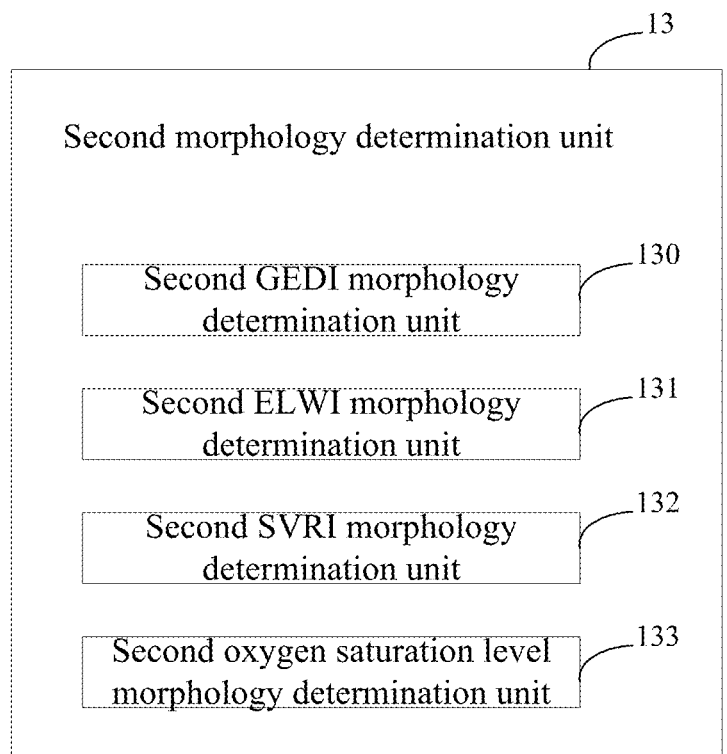
FIG. 9 is a schematic structural diagram of a second morphology determination unit in FIG. 6.

Referring to FIG. 9, the second morphology determination unit 13 may further include at least one of:

a second GEDI morphology determination unit 130 for determining a second size corresponding to the cardiac contour in the corresponding simulated graph, according to a second monitoring value of the global end-diastolic volume index (GEDI);

a second ELWI morphology determination unit 131 for determining a second height corresponding to the height of the horizontal plane of the lung water in the corresponding simulated graph, according to the second monitoring value of the extravascular lung water index (ELWI);

a second SVRI morphology determination unit 132 for determining a second diameter corresponding to the tubular cross-section in the corresponding simulated graph according to the second monitored value of the systemic vascular resistance index (SVRI); and a second oxygen saturation level morphology determination unit 133 for determining a second color corresponding to the blood vessel, in the corresponding simulated graph according to the second monitoring value of the oxygen saturation level.

Figure 10:
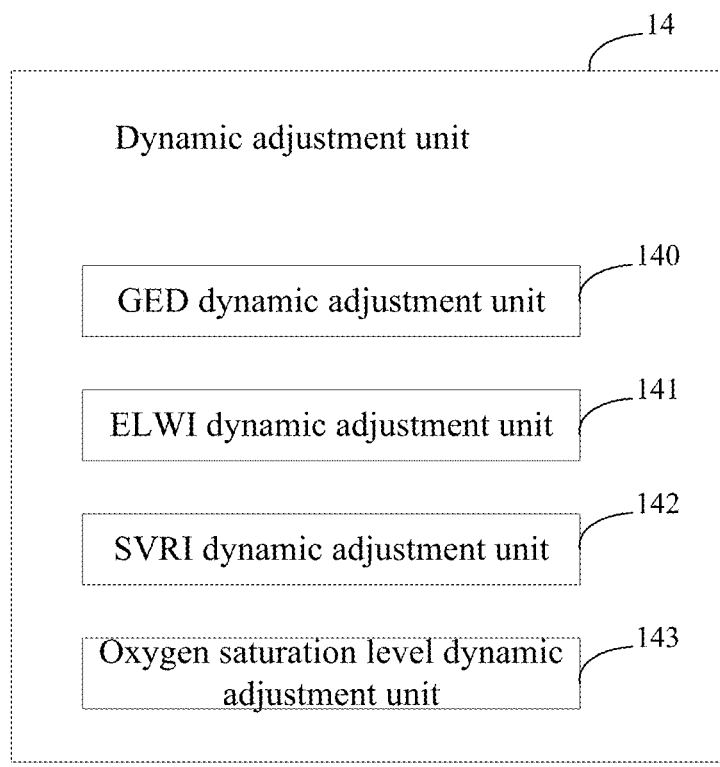
FIG. 10 is a schematic structural diagram of a dynamic adjustment unit in FIG. 6.

Referring to FIG. 10, the dynamic adjustment unit 14 may further include at least one of:

a GED dynamic adjustment unit 140 for dynamically adjusting the size of the cardiac contour from the first size to the second size, in the simulated graph corresponding to the global end-diastolic volume index (GED);

an ELWI dynamic adjustment unit 141 for dynamically adjusting the height of the horizontal plane of the lung water from the first height to the second height, in the simulated graph corresponding to the extravascular lung water index (ELWI);

an SVRI dynamic adjustment unit 142 for dynamically adjusting the diameter of the tubular cross-section from the first diameter to the second diameter, in the simulated graph corresponding to the systemic vascular resistance index (SVRI); and an oxygen saturation level dynamic adjustment unit 143 for dynamically adjusting a color of the blood vessel from the first color to the second color, in the simulated graph corresponding to the oxygen saturation level. Specifically, the dynamic adjustment may be implemented through animation.

For more details, reference may be made to the above description of FIGS. 1 to 4C, which are not repeated here.

Accordingly, the present disclosure further provides a monitor, which includes at least the system for dynamically displaying a change of a parameter measured at an interval described above with reference to FIGS. 5 to 9, the details of which will not be repeated here.

In summary, by implementing various embodiments of the present disclosure, the following beneficial effects can be achieved. The present disclosure provides a method and a system for dynamically displaying a change of a parameter measured at an interval, in which a simulated graph of each type of hemodynamic parameter is provided on a graphic display interface, and the difference between a previous monitored value and a current monitored value of the hemodynamic parameter at different intervals is shown through changes of shape, color, height and the like in the simulated graph. In this way, medical care personnel can visually and quickly grasp the change of the patient's hemodynamic parameter at different intervals by viewing the graphic display interface, which can assist in determining therapeutic effects on the patient before and after the treatment.

Furthermore, a reference morphology corresponding to the normal value of each hemodynamic parameter is marked on each simulated graph, so as to further provide a reference indication to the medical care personnel.

All or some of the procedure of the exemplary methods described above could be achieved by hardware commanded by a computer program, which program can be stored in a computer-readable storage medium and when executed by a processor, carry out a procedure as shown in the embodiments of the methods described above. The storage medium can be a magnetic disk, an optical disk, a read-only memory (ROM) or a random access memory (RAM), etc.

The technical features or operating steps illustrated in the embodiments of the present disclosure can be combined in any suitable way. Those of ordinary skill in the art will understand that the sequence of steps or actions in the methods illustrated by the embodiments of the present disclosure can be altered. Therefore, unless a certain sequence is specifically required, any sequence in the accompanying drawings or the detailed description is merely for the purpose of illustration and not obligatory.

Disclosed above are some embodiments of the present disclosure and should not be taken as limiting of the claimed scope of the present disclosure. Therefore, any equivalent changes remain within the scope covered by the present disclosure.

What is claimed is:

1. A method for dynamically displaying a change of a parameter measured at an interval, comprising:

dynamically monitoring a type of hemodynamic parameter of a patient by means of a sensor on a monitor and storing the type of hemodynamic parameter monitored;

obtaining a first monitoring value of the type of hemodynamic parameter monitored at a first monitoring time;

configuring a simulated graph corresponding to the type of hemodynamic parameter on a graphic display interface, and correspondingly displaying a first morphology of the simulated graph according to the first monitoring value of the type of hemodynamic parameter monitored;

obtaining a second monitoring value of the type of hemodynamic parameter monitored at a second monitoring time, and determining a second morphology of the corresponding simulated graph according to the second monitoring value; and dynamically adjusting the simulated graph corresponding to the type of hemodynamic parameter monitored from the first morphology to the second morphology on the graphic display interface;

wherein the hemodynamic parameter comprises an oxygen saturation level, and wherein the simulated graph corresponding to the oxygen saturation level is configured as a blood vessel graph, wherein various monitoring values of the oxygen saturation level correspond to various respective colors of blood vessels in the blood vessel graph; and wherein the method further comprises:

predetermining a normal value of the type of hemodynamic parameter, configuring a reference morphology according to the normal value of the type of hemodynamic parameter, and statically marking said reference morphology in the simulated graph displayed in the first morphology or the second morphology corresponding to the type of hemodynamic parameter.

2. The method of claim 1, wherein the hemodynamic parameter further comprises at least one of a global end-diastolic volume index (GEDI), a systemic vascular resistance index (SVRI), and an extravascular lung water index (ELWI), wherein:
the simulated graph corresponding to the global end-diastolic volume index (GEDI) is configured as a cardiac contour graph;
the simulated graph corresponding to the extravascular lung water index (ELWI) is configured as a lung graph with lung water; and
the simulated graph corresponding to the systemic vascular resistance index (SVRI) is configured as a tubular structure.

3. The method of claim 2, wherein configuring a simulated graph corresponding to the type of hemodynamic parameter on a graphic display interface and displaying a first morphology of the corresponding simulated graph according to the first monitoring value of the type of hemodynamic parameter monitored comprises at least one of following steps:
adjusting a size of the cardiac contour in the corresponding simulated graph to a corresponding first size, according to the first monitoring value of the global end-diastolic volume index (GEDI), and displaying the first size of the cardiac contour;
adjusting a height of a horizontal plane of the lung water in the corresponding simulated graph to a corresponding first height, according to the first monitoring value of the extravascular lung water index (ELWI), and displaying the first height of the horizontal plane of the lung water;
adjusting a diameter of the tubular structure in the corresponding simulated graph to a corresponding first diameter, according to the first monitoring value of the systemic vascular resistance index (SVRI), and displaying the first diameter of the tubular structure; and
adjusting a color of the blood vessel in the corresponding simulated graph to a corresponding first color, according to the first monitoring value of the oxygen saturation level, and displaying the first color of the blood vessel.

4. The method of claim 3, wherein determining a second morphology of the corresponding simulated graph according to the second monitoring value comprises at least one of the following steps:
determining a second size of the cardiac contour in the corresponding simulated graph, according to the second monitoring value of the global end-diastolic volume index (GEDI);
determining a second height of the height of the horizontal plane of the lung water in the corresponding simulated graph, according to the second monitoring value of the extravascular lung water index (ELWI);
determining a second diameter of the tubular structure in the corresponding simulated graph, according to the second monitoring value of the systemic vascular resistance index (SVRI); and
determining a second color of the blood vessel in the corresponding simulated graph, according to the second monitoring value of the oxygen saturation level.

5. The method of claim 4, wherein the dynamic adjustment is implemented through animation, and wherein dynamically adjusting the simulated graph from the first morphology to the second morphology on the graphic display interface comprises at least one of the following steps:
dynamically adjusting the size of the cardiac contour from the first size to the second size, in the simulated graph corresponding to the global end-diastolic volume index (GEDI);
dynamically adjusting the height of the horizontal plane of the lung water from the first height to the second height, in the simulated graph corresponding to the extravascular lung water index (ELWI);
dynamically adjusting the diameter of the tubular structure from the first diameter to the second diameter, in the simulated graph corresponding to the systemic vascular resistance index (SVRI); and
dynamically adjusting the color of the blood vessel from the first color to the second color, in the simulated graph corresponding to the oxygen saturation level.

6. The method of claim 2, wherein when the type of hemodynamic parameter is GEDI, the method comprises:
configuring another cardiac contour graph by a dashed line as the reference morphology corresponding to GEDI, and
marking the another cardiac contour graph by the dashed line in the cardiac contour graph as the simulated graph corresponding to the GEDI.

7. The method of claim 2, wherein when the type of hemodynamic parameter is SVRI, the method comprises:
configuring a tubular structure with constant diameter as the reference morphology corresponding to SVRI.

8. The method of claim 1, further comprising:
prestoring various morphologies of each simulated graph corresponding to the monitoring values of the type of hemodynamic parameter.

9. The method of claim 1, further comprising:
presetting a time interval between the first monitoring time and the second monitoring time, and after one dynamic adjustment, automatically performing a next dynamic adjustment when the time interval is reached.

10. The method of claim 1, further comprising:
manually determining the first monitoring time and the second monitoring time.

11. A dynamic monitor, comprises:
a dynamic monitoring unit for dynamically monitoring a type of hemodynamic parameter of a patient by means of a sensor, and storing the type of hemodynamic parameter monitored;
a first monitoring value obtaining unit for obtaining a first monitoring value of the type of hemodynamic parameter monitored at a first monitoring time;
a first morphology display unit for configuring a simulated graph corresponding to the type of hemodynamic parameter on a graphic display interface and displaying a first morphology of the corresponding simulated graph according to the first monitoring value of the type of hemodynamic parameter monitored;
a second morphology determination unit for obtaining a second monitoring value of the type of hemodynamic parameter monitored at a second monitoring time and determining a second morphology of the corresponding simulated graph according to the second monitoring value; and
a dynamic adjustment unit for dynamically adjusting the simulated graph corresponding to the type of hemodynamic parameter monitored from the first morphology to the second morphology on the graphic display interface;

wherein the dynamic monitor further comprises a reference morphology marking unit predetermining a normal value of the type of hemodynamic parameter, configuring a reference morphology according to the normal value of the type of hemodynamic parameter and statically marking said reference morphology in the simulated graph displayed in the first morphology or the second morphology corresponding to the type of hemodynamic parameter.

12. The dynamic monitor of claim 11, wherein the hemodynamic parameter comprises at least one of a global end-diastolic volume index (GEDI), a systemic vascular resistance index (SVRI), and an extravascular lung water index (ELWI), wherein:
   the simulated graph corresponding to the global end-diastolic volume index (GEDI) is configured as a cardiac contour graph;
   the simulated graph corresponding to the extravascular lung water index (ELWI) is configured as a lung graph with lung water; and
   the simulated graph corresponding to the systemic vascular resistance index (SVRI) is configured as a tubular structure graph.

13. The dynamic monitor of claim 12, wherein the first morphology display unit comprises at least one of:
   a GEDI simulated display unit for adjusting a size of the cardiac contour in the corresponding simulated graph to a corresponding first size, according to the first monitoring value of the global end-diastolic volume index (GEDI) and displaying the first size of the cardiac contour;
   an ELWI simulated display unit for adjusting a height of a horizontal plane of the lung water in the corresponding simulated graph to a corresponding first height, according to the first monitoring value of the extravascular lung water index (ELWI) and displaying the first height of the horizontal plane of the lung water;
   a SVRI simulated display unit for adjusting a diameter of the tubular structure in the corresponding simulated graph to a corresponding first diameter, according to the first monitoring value of the systemic vascular resistance index (SVRI) and displaying the first diameter of the tubular structure; and
   an oxygen saturation level simulated display unit for adjusting a color of the blood vessel in the corresponding simulated graph to a corresponding first color, according to the first monitoring value of the oxygen saturation level and displaying the first color of the blood vessel.

14. The dynamic monitor of claim 13, wherein the second morphology determination unit comprises at least one of:
   a second GEDI morphology determination unit for determining a second size of the cardiac contour in the corresponding simulated graph, according to the second monitoring value of the global end-diastolic volume index (GEDI);
   a second ELWI morphology determination unit for determining a second height of the height of the horizontal plane of the lung water in the corresponding simulated graph, according to the second monitoring value of the extravascular lung water index (ELWI);
   a second SVRI morphology determination unit for determining a second diameter of the tubular structure in the corresponding simulated graph, according to the second monitoring value of the systemic vascular resistance index (SVRI); and
   a second oxygen saturation level morphology determination unit for determining a second color of the blood vessel in the corresponding simulated graph, according to the second monitoring value of the oxygen saturation level.

15. The dynamic monitor of claim 14, wherein the dynamic adjustment unit implements the dynamic adjustment through animation; and wherein the dynamic adjustment unit comprises at least one of:
   a GEDI dynamic adjustment unit for dynamically adjusting the size of the cardiac contour from the first size to the second size, in the simulated graph corresponding to the global end-diastolic volume index (GEDI);
   an ELWI dynamic adjustment unit for dynamically adjusting the height of the horizontal plane of the lung water from the first height to the second height, in the simulated graph corresponding to the extravascular lung water index (ELWI);
   a SVRI dynamic adjustment unit for dynamically adjusting the diameter of the tubular structure from the first diameter to the second diameter, in the simulated graph corresponding to the systemic vascular resistance index (SVRI); and
   an oxygen saturation level dynamic adjustment unit for dynamically adjusting the color of the blood vessel from the first color to the second color, in the simulated graph corresponding to the oxygen saturation level.

16. The dynamic monitor of claim 12, wherein when the type of hemodynamic parameter is GEDI, the reference morphology is another cardiac contour graph marked by a dashed line.

17. The dynamic monitor of claim 12, wherein when the type of hemodynamic parameter is SVRI, the reference morphology is a tubular structure with constant diameter.

18. The dynamic monitor of claim 11, further comprises at least one of:
   a storage unit for prestoring various morphologies of the simulated graphs corresponding to the monitoring values of the type of hemodynamic parameter;
   a time interval setting unit for presetting a time interval between the first monitoring time and the second monitoring time, and after one dynamic adjustment, automatically performing a next dynamic adjustment when the time interval is reached; and
   a monitoring time setting unit for manually determining the first monitoring time and the second monitoring time.

* * * * *